(12) United States Patent
Lucic et al.

(10) Patent No.: US 8,470,258 B2
(45) Date of Patent: Jun. 25, 2013

(54) SURFACE-STRUCTURED DEVICE FOR LIFE-SCIENCE APPLICATIONS

(75) Inventors: Ivan Lucic, Vienna (AT); Harald Kraushaar, Salzburg (AT)

(73) Assignee: Sony DADC Austria AG, Anif (AT)

( * ) Notice: Subject to any disclaimer, the term of this patent is extended or adjusted under 35 U.S.C. 154(b) by 275 days.

(21) Appl. No.: 12/852,841

(22) Filed: Aug. 9, 2010

(65) Prior Publication Data
US 2011/0104732 A1 May 5, 2011

(30) Foreign Application Priority Data
Aug. 13, 2009 (EP) .................................. 09010463

(51) Int. Cl.
*G01N 1/28* (2006.01)
*B01L 3/00* (2006.01)

(52) U.S. Cl.
USPC ........... 422/402; 422/502; 422/552; 436/177; 436/178; 428/141; 428/156

(58) Field of Classification Search
USPC ... 422/402, 502, 552; 436/177, 178; 428/141, 428/156
See application file for complete search history.

(56) References Cited

U.S. PATENT DOCUMENTS

| | | | |
|---|---|---|---|
| 2005/0095699 A1 | 5/2005 | Miyauchi et al. | |
| 2005/0214935 A1 | 9/2005 | Kuwabara et al. | |
| 2006/0183222 A1 | 8/2006 | Kuwabara et al. | |
| 2006/0281172 A1 | 12/2006 | Kuwabara et al. | |
| 2007/0134787 A1 | 6/2007 | Shirakawabe et al. | |
| 2007/0218554 A1 | 9/2007 | Miyake et al. | |
| 2007/0243607 A1 | 10/2007 | Cheng et al. | |
| 2009/0155730 A1 | 6/2009 | Shirasagi | |
| 2009/0246470 A1 | 10/2009 | Lucic et al. | |

FOREIGN PATENT DOCUMENTS

| | | |
|---|---|---|
| EP | 2106858 | * 10/2009 |
| WO | WO 2007/026294 A1 | 3/2007 |
| WO | WO 2008/066965 A2 | 6/2008 |
| WO | WO 2008/140295 A1 | 11/2008 |

OTHER PUBLICATIONS

Extended European Search Report issued Jan. 22, 2010 in EP 09 01 0463.

J. Heitz, et al., "Cell Adhesion on polytetrafluoroethylene modified by UV-irradiation in an ammonia atmosphere", Wiley Periodicals, Inc., Published online Aug. 2003, pp. 130-137.

(Continued)

*Primary Examiner* — Lyle Alexander
(74) *Attorney, Agent, or Firm* — Oblon, Spivak, McClelland, Maier & Neustadt, L.L.P.

(57) ABSTRACT

Embodiments of the invention relate a surface-structured device for life-sciences and a life-science method applying the surface-structured device. The surface-structured device has a substrate with a frontside surface corresponding to a first surface; and a plurality of protrusions arranged on the frontside surface. A shortest dimension of the protrusions at the junction from the protrusion to the front-side surface is smaller than 250 nm and at least a first group of the plurality of protrusions is arranged on a first planar area of the frontside surface in a first regular pattern in a plane of the first planar area of the frontside surface. Further embodiments relate to a stamper which may be used in the manufacturing method of the surface-structured device and a manufacturing method for surface-structured device.

14 Claims, 5 Drawing Sheets

OTHER PUBLICATIONS

Esther Rebollar, et al., "Proliferation of aligned mammalian cells on laser-nanostructured polystyrene", Biomaterials, 2008, pp. 1-11.

Won-Gun Koh, et al., "Control of Mammalian Cell and Bacteria Adhesion on Substrates Micropatterned with Poly(ethylene glycol) Hydrogels", Biomedical Microdevices, vol. 5, No. 1, 2003, pp. 11-19.

Natanel Korin, et al., "A parametric study of human fibroblasts culture in a microchannel bioreactor", The Royal Society of Chemistry 2007, Lab Chip, vol. 7, 2007, pp. 611-617.

Alain Walcarius, et al., "Exciting new directions in the intersection of functionalized sol-gel materials with electrochemistry", The Royal Society of Chemistry 2005, Journal of Materials Chemistry, vol. 15, 2005, pp. 3663-3689.

Regina Mikulikova, et al., "Cell microarrays on photochemically modified polytetrafluoroethylene", Biomaterials, vol. 26, 2005, pp. 5572-5580.

Michael Olbrich, et al., "Electroporation chip for adherent cells on photochemically modified polymer surfaces", Applied Physics Letters, vol. 92, No. 013901, 2008, pp. 1-3.

Thomas Peterbauer, et al., "Simple and versatile methods for the fabrication of arrays of live mammalian cells", The Royal Society of Chemistry 2006, Lab on a Chip, vol. 6, 2006, pp. 857-863.

Cornelia Pahle MD, "Different role of ligand binding affinity and cytoskeleton mounting in $\alpha_{IIb}\beta_3$ (GPIIb/IIIa)-mediated cell aggregation and adhesion", Promotion Department of Internal Medicine, 2003, 5 pages (with English translation).

F. Seilern-Aspang, "The cell degeneration as development-physiological problem", Die Naturwissenschaften, 1961, 3 pages (with English translation).

M. Kientzler, et al., "To the support of the cell aggregate ions in *Polysphondylium pallidum* through light", Institute for biology of the University of Tübingen, Aug. 12 and Sep. 27, 1971, 3 pages (with English translation).

D. Seitz, et al., "Patterned Nanostructures as Surface Modifications for Enhanced Cell Adhesion", Strategies in Tissue Engineering, Cytotherapy, vol. 8, 2006, pp. 44-45 (with BioCer/FBI Summary Sheet).

* cited by examiner

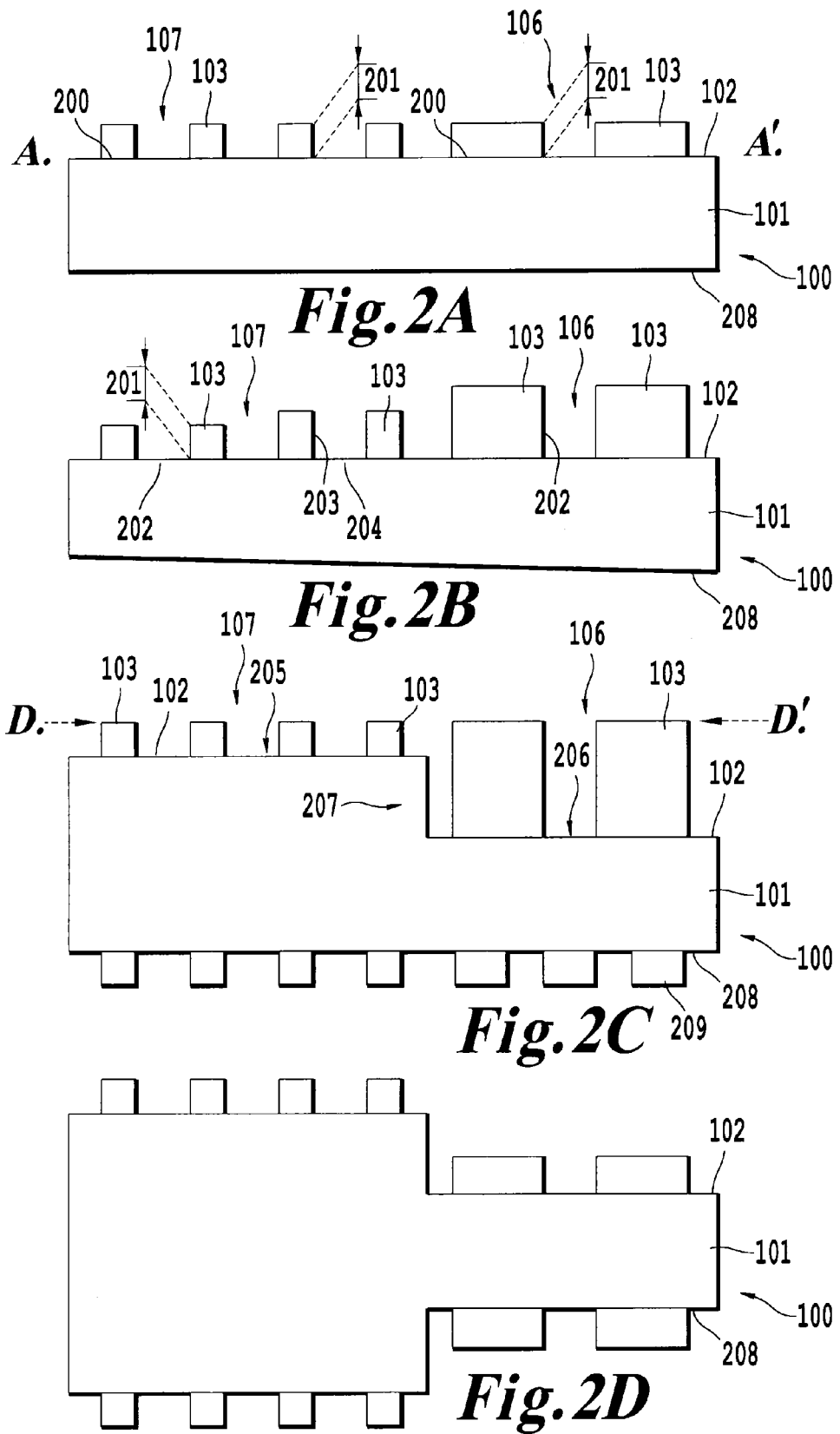

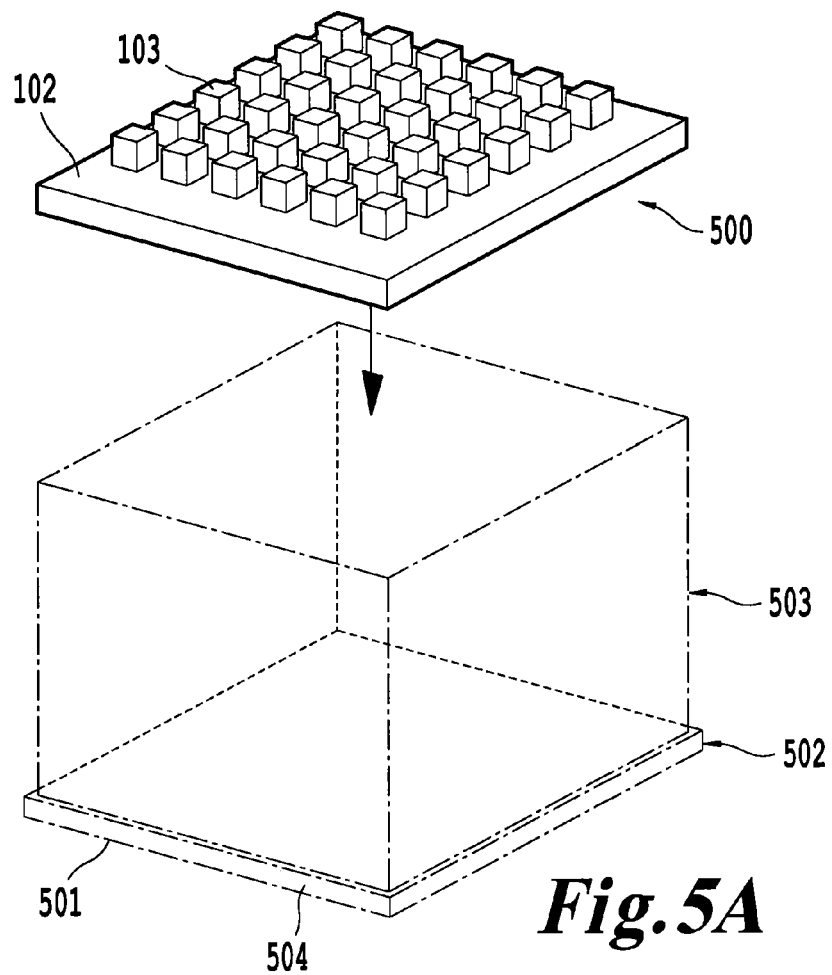
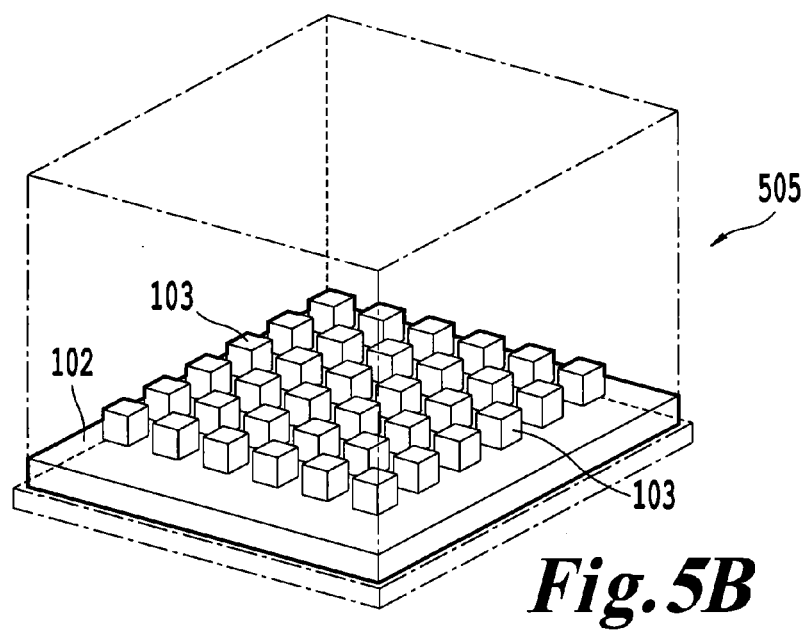

SURFACE-STRUCTURED DEVICE FOR LIFE-SCIENCE APPLICATIONS

Embodiments of the invention relate to a surface-structured device for life-science applications, a stamper used for manufacturing the surface-structured device, a life-science method applying the surface-structured device and a manufacturing method for the surface-structured device.

BACKGROUND

Microbiological manipulation is often conducted using a liquid phase and/or a gel phase. This often requires the usage of vessels. The walls of such vessels or inlays in such vessels, however, may not only have the effect of keeping the sample in the vessel, but there may be as well an interaction of the microbiological sample with the surfaces exposed to a sample liquid. Such an interaction may be intended to achieve a specific effect or the interaction may be not wanted. In the latter case the unwanted interaction, however, is a direct result of the fact that the contact between the liquid and the sample material within the liquid to the surfaces of the vessel cannot be avoided and, therefore, the interaction cannot be circumvented.

For example, adhesion of microbiological material, e.g. cells during cell growth or tissue engineering, to the surface may have an impact in the manipulation results of the microbiological samples.

Therefore, providing vessels with a surface functionality adapted to the problem of the individual microbiological method, for example a manipulation of cells or growth of cells, is often a technical challenge. Further, these vessels are normally used only once, for example to avoid cross contamination. Therefore, the vessels must not be expensive and consequently there is a need for simple manufacturing methods allowing a high throughput manufacturing method.

BRIEF SUMMARY

It is an object of the embodiments to provide a surface-structured device for manipulations in life-sciences, a stamper used for manufacturing the surface-structured device, a life-science method applying the surface-structured device and a manufacturing method for the surface-structured device.

This object is solved by a surface-structured device for life-science methods, a stamper used for manufacturing the surface-structured device, a life-science method, and a manufacturing method for the surface-structured device according to the present disclosure.

Further details will become apparent from a consideration of the drawings and ensuing description.

BRIEF DESCRIPTION OF THE SEVERAL VIEWS OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIGS. 2a to 2d show schematically different embodiments in a vertical cut along the line indicated by A-A' in FIG. 1;

FIG. 5a shows schematically an embodiment of the surface-structured device as an inlay;

FIG. 5b shows schematically an embodiment of the surface-structured device as an integral part of a vessel;

DETAILED DESCRIPTION

In the following, embodiments are described. It is important to note, that all described embodiments in the following may be combined in any way, i.e. there is no limitation that certain described embodiments may not be combined with others. Further, it should be noted that same reference signs throughout the figures denote same or similar elements.

It is to be understood that other embodiments may be utilized and structural or logical changes may be made without departing from the scope of the invention. The following detailed description, therefore, is not to be taken in a limiting sense, and the scope of the present invention is defined by the appended claims.

It is to be understood that the features of the various embodiments described herein may be combined with each other, unless specifically noted otherwise.

Figure 1:
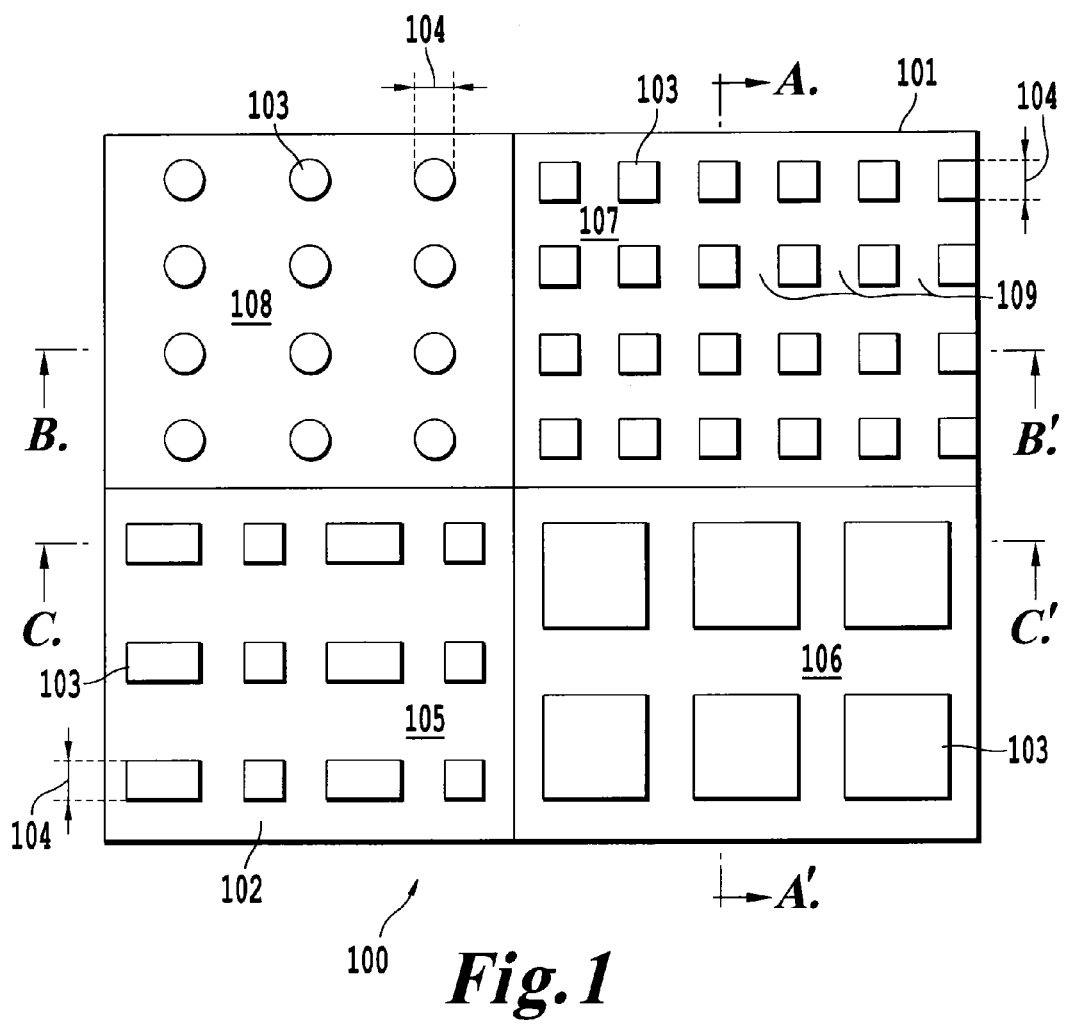
FIG. 1 shows schematically an embodiment of a surface-structured device in a view vertical to the frontside plane.

In FIG. 1, a surface-structured device 100 for life-science methods according to an embodiment is shown.

The term life-science methods or applications or manipulations is used in a broad meaning of any biological application and comprises microbiological, large-scale biotechnological, medical or pharmaceutical methods or applications or manipulations. The life science methods or applications or manipulations may further be conducted in research activities or other analysis or testing applications.

The surface-structured device may include a substrate 101 with a frontside surface 102. The frontside surface 102 corresponds to a first surface of the substrate 101.

The material of a surface layer of the substrate 101 towards the frontside surface 102 may comprise a polymer, a treated polymer, a metal or an alloy. A treated polymer may be a polymer treated by at least one or more treatment methods from the group of plasma-exposure, $\gamma$-exposure, or UV-exposure treatment, chemical treatment or biochemical treatment. The polymers may be polystyrene, polycarbonate, polypropylene, polymethyl methacrylate (PMMA), cyclic oligophosphates, cyclic oligocarbonates, cyclic olefin polymers, cyclic olefin copolymers or any derivative of these polymers or any combinable copolymers of these polymers. The material may be a polycarbonate. The thickness of the surface layer is preferably below 250 nm or even below 50 nm. The material of the surface layer may as well be different in different areas of the frontside surface 102.

Below the surface layer a further substrate layer or layers may be provided and the substrate may be have a multilayer structure. The material and the thickness of surface layer may provide the required stability to the surface-structured device.

The substrate layer may have at least a two layer structure comprising the surface layer and the substrate layer. The substrate layer below the surface layer may be defined independently from a possible interaction of the surface of the surface-structured device 100 with a biological sample in a life-science method. Thus, the substrate layer may provide the stability, the substrate layer may be provided on the opposite side to the surface layer with a shape that is adapted to a further device on which the surface-structured device 100 may be positioned, the thermal extension of the surface-structured device 100 may be controlled by the substrate layer or the substrate layer may be used for any other adaptation to the external requirements. Therefore, the substrate layer provides a large flexibility to adapt the surface-structured device 100 to the external factors.

On the frontside surface 102 of the surface-structured device 100 a plurality of protrusions 103 are arranged. A protrusion is an elevation of material over a surface to which the elevation is in direct contact.

At the junctions 200, see FIGS. 2a and 2b, from the protrusions 103 to the front-side surface 102 of the substrate 101 the composition of the material of the protrusions 103 may be at least partially the same as the composition of the material of the surface layer of the substrate 101. The material of the protrusions 103 in another embodiment may entirely have the same composition as the material of the surface layer of the substrate 101. The material of the protrusion may as well be different in different areas of the frontside surface 102.

The selection of suitable materials may, therefore, be based on optimizing the manufacturing process and on the intended use of the surface-structured device 100.

A shortest dimension 104 of the protrusions 103 at the junction 200 from the protrusion 102 to the frontside surface 102 may have any size smaller than 250 nm. A lower limit may be 50 nm, however, even sizes below 50 nm may be used in the future. New technical developments may allow correspondingly to reduce the smallest size further.

The shortest dimension 104 describes the shortest distance between two opposite sides of a protrusion 103 on the level of the frontside surface 102 (footprint). For a circular footprint this is the diameter of the circle. For a person skilled in the art it would be obvious that due to the patterning process, for example by footing (rounded transition from the side wall of the protrusion to the bottom surface of the open area between the protrusions) or underetching, the real footprint may be to be determined by extrapolation. Thus, the size of the protrusions 103 may to be larger or smaller in the plane of frontside surface 102, but the person skilled in the art would know how to correct for these manufacturing artifacts and to determine the shortest dimension 104 by extrapolating of the flanks of the protrusions 103.

In further embodiments protrusions 103 may have quadratic, rectangular, rectangular with rounded corners, oval or a round footprints at the junction 200 to the substrate. In embodiments with protrusions having a longer dimension vertical to the shorter dimension, the length of the longer dimension may be 1.5 times, 2 times, 2.5 times, 3 times, 3.5 times, 4 times or 4.5 times the shortest dimension of the protrusion.

The interaction between protrusions having a smallest dimension smaller than 250 nm may allow achieving very specific and unexpected results, when brought in contact with biological material according to life-science methods. Further, the shortest dimension smaller than 250 nm allows the application of the manufacturing processes known for the Blu-ray disc manufacturing and, therefore, represent a special range of possible shortest dimensions.

The terms biological material/sample/sample material corresponds to any biological material which may be used in any life-science methods. Embodiments of these methods are the above-described areas of life-science methods or applications or manipulations and the more specific embodiments of the life-science methods in the following parts of the description.

The protrusions 103 of at least a first group of the plurality of protrusions 103 may be arranged on a first planar area 105, 106, 107, 108 of the frontside surface 102 in a first regular pattern in a plane of the first planar area 105, 106, 107, 108 of the frontside surface 102.

A regular pattern may be any pattern with symmetry in the positioning of the protrusions 103 on the frontside surface 102. The protrusions 103 themselves may be isolated from each other or may be in contact to each other. In embodiments with protrusions in contact to each other a grating or a net or spiral may be formed by the protrusions. The protrusions 103 may have the identical footprint within an area 106, 107, 108 with a regular pattern or the footprint may differ in an area 105 with a regular pattern.

The symmetry of the regular pattern in a first direction in the planar area plane may be different or the same than/as the symmetry the regular pattern in a second direction in the planar area plane vertical to the first direction.

The regular pattern in a first direction in the planar area plane may be different or the same than/as the regular pattern in a second direction in the planar area plane vertical to the first direction.

The symmetry may as well be a two dimensional regular pattern in the planar area plane. In an embodiment the two dimensional symmetry may a spiral, in another embodiment the protrusions may be arranged in circles with different radii having the same center point.

Within a regular pattern the average distance 109 defined as the distance between the center of two neighboring protrusions divided by 2 (half pitch) may have any value equal or above the smallest dimension 104. The half pitch may be between 1 times and 5 times the size of the shortest dimension.

The size of the distance between two neighboring protrusions may have any size. The size of the distance between two neighboring protrusions, corresponding to the opening between two neighboring protrusions, may be between 1 times and 10 times the size of the shortest dimension.

The regular pattern may have the effect that by using a pattern which is identical in two vertical directions of the area 105, 106, 107, 108 plane, no preferred direction arises during the life-science method and only the shape of the protrusions 103 and the regular pattern impacts the results of the life-science method. This may be especially relevant, when the surface of the protrusions 103 is functionalized or when the adhesion or separation to the specific regular pattern is the parameter, which impacts the life-science method. Thus, an interaction between the biological sample and the protrusions 103 may be maximized. Embodiments of this use of the surface-structured device 100 may be cell cultivation methods, cell growth methods, cell immobilization methods, cell separation/selection methods or other cell manipulation and/or cell management methods. The immobilizaion may allow cell-managing like cell staining, cell internal process analysis, chromosome analysis or any other application using genetical or molecular biological methods. One further use may be a cell tissue growth step. A use may include the step of fixing oral mucosa cells to the structured surface. Another use may comprise the step of separation of epithelial cells for bio-dressing, separation of cancer cells from other cells out of the mixed samples.

It is noted that a life-science method applying any of the embodiments of the surface-structured device may comprise at least one step of a life-science method in which a processing surface is accessible for a sample material of the life-science method and the processing surface is a surface with protrusions 103 in a regular pattern as described for the surface-structured device 100.

Such a pattern which is identical in two vertical directions of the area 105, 106, 107, 108 plane, wherein the protrusions 103 form gratings may especially be suited for use in the cell tissue-engineering to obtain e.g. isotropic tissues in the tissue plane.

In other embodiments a regular pattern may include in one direction a different regularly repeating structure than in the corresponding vertical direction. Such embodiments of the surface-structured device 100 may be preferably used in a life-science method requiring a flow direction of a sample liquid, a cell growth direction or a cell tissue growth direction.

The area 105, 106, 107, 108 may be a planar area of the frontside surface 102.

The size of the area 105, 106, 107, 108 may be at least more than 1000 mm$^2$, in other embodiments more than 2000 mm$^2$, and have a rectangular shape. In other embodiments the area 105, 106, 107, 108 may have much smaller sizes below 100 mm$^2$ or even below 20 mm$^2$.

This has the effect that the large sized areas allow to use large volumes and a large amount of sample material. Smaller sized areas on separate substrates may be housed for example in many reaction chambers in one vessel allowing a high through-put screening.

The smaller sized areas may as well be used in devices, which have only limited space such as mobile devices. The smaller sized areas may further be used in the analysis of traces of a biological material, since locating of biological material is easier in a smaller volume.

In another embodiment the surface-structured device 100 may have a plurality of groups of the plurality of protrusion 103, each of the further groups may be formed in different areas 105, 106, 107, 108 of the frontside surface 102. Each of the different areas 105, 106, 107, 108 may be planar and parallel to each other. The protrusions 103 of each of the groups may be arranged in a regular pattern in a plane of the corresponding different area 105, 106, 107, 108. The number of groups may vary form 2 to several 100.

It is obvious that in any of the life-science methods described above any the surface-structured devices 100 may be used. The size of the effect may differ, however, there may be as well other reasons for using the surface-structured device 100 not exhibiting the maximal achievable effect such as economical reasons or operational reasons.

In one embodiment, the regular patterns may be different from each other for each group or for some groups.

In another embodiment, the regular pattern may be the same for each of the plurality of groups. These groups may be separated by areas without protrusions 103.

Each individual group of protrusions 103 in one of the corresponding area 105, 106, 107, 108 may have the characteristics, which has been described above referring to the at least first group of protrusions 103.

In another embodiment, additional groups of a plurality of protrusions with the same characteristics as described above referring to the at least first group of protrusions 103 may be present in further areas additionally to an area with the first group protrusions 103, differing from the first group of protrusions 103 only in that the smallest dimension is larger than 250 nm.

All embodiments may further comprise an area without protrusions and this area may be of the same size as the areas 105, 106, 107, 108 with protrusions 103. This allows determining in parallel the effect of the protrusions on the life-science method.

The combination of areas with different regular patterns allows the separation of different types of biological material, for example different types of cells, due to the different interaction between the structured surface and the cells. The different interaction may be a different adhesion ratio of attached cells to a surface having protrusions and not attached cells to the surface having protrusions, wherein the adhesion ratio is a function of protrusion dimension and protrusion shape. Thus, such a surface-structured device may be used in a chromatographic separation method. Another embodiment for the use of the structured-device for separation may be a cell cultivation method in which the cells predominantly reproduce in an attached state and, therefore, the strongest reproduction is obtained in the areas with the strongest adhesion. In another embodiment for the use of the structured-device the cell cultivation may be combined with the separation effect in that the cells have different adhesion ratios on the differently shaped and/or sized protrusions and are cultivated with the highest proliferation rate on the corresponding area.

Further, different embodiments may have various heights of the protrusions 103 and the frontside surface 102 direction vertical to frontside surface 102.

Such embodiments are shown in FIGS. 2a to 2d, which show a vertical cut along the line indicated in FIG. 1 by A and A'.

The height 201 of the protrusions 103 may be the same in the different areas 106, 107. Further, the aspect ratios of the protrusions 103 may be different in different areas 106, 107. This is shown in FIG. 2a.

Further, a height 201 of protrusions 103 in a first sub-area 202 and a height 203 of protrusions 103 in a second sub-area 204, the first sub-area 202 and the second sub-area 204 belonging to the first area 107 with a regular pattern, may be different. This is shown in FIG. 2b.

There may exist a plurality of such sub-areas within the first area 107 having protrusions with different heights.

The height of the protrusion may be preferably in the range between 10 nm and 100 nm. Higher and lower protrusions may as well be present.

In another embodiment the surface frontside 102 may be separated in different height areas 205, 206, which are parallel to each other, but may be located in different planes. The different height areas 205, 206 may separated by connecting wall vertically to the height areas 205, 206 and having a step height difference 207. This is shown in FIG. 2c.

In one embodiment each area 107, 106 with a different regular pattern may correspond to one height area 205, 206. This is shown in FIG. 2c.

In a further embodiment, the top of the protrusions 103 arranged in at least two height areas 205, 206 may be located within one plane indicated in FIG. 2c by D-D' parallel to the height areas 205, 206. This is shown in FIG. 2c.

In a further embodiment, a surface-structured device may have a plurality of height areas being parallel and within different planes and the top of all protrusions may be located within one plane parallel to the height areas.

By selecting an appropriate height of the protrusions for a given regular pattern the aspect ratio of the protrusions may be varied. This has the effect that the stability of the protrusion during a manufacturing process and during life-science processing may be ensured. Further, the height may have an impact on the interaction with the biological sample, and, therefore, the height represents a further parameter, which may be selected to optimize any of the life-science methods described above. Another effect of the height of the protrusions may be the velocity with which a liquid of the biological sample may flow over the surface-structure device. These effects may be controlled in similar manner by selecting the step height difference between the different parallel areas and, further, by the selected height of the protrusions and the step height difference between the different parallel areas. Especially, latter may allow the optimization of the stability of the protrusions on the substrate of the surface-structured device.

The effect of controlled flow of liquids may be achieved by the usage of surface-structured devices with a substrate in which channels are formed and whith the protrusions being arranged on at least one surfaces of the channels. In one embodiment only on the bottom surface of the channels protrusions are arranged. In another embodiment protrusions are arranged on all surfaces of the channels. Thus, the trade off between manufacturing complexity and the size of the surface effect on the biological sample may be adjusted corresponding to the use of the surface-structured device.

In another embodiment channels may be formed by lengthy protrusions. Further protrusions may be placed between the lengthy protrusions. Between the lengthy protrusions opening may be provided. This may have the further effect that the corresponding structures or on the master device, or on the stamper, or on the surface-structured device are stabilized as the tension within the structures are reduced and a two-dimensional net is formed on the stamper, instead of separated areas.

In FIGS. 2c and 2d an embodiment having protrusions on a backside surface 208 of the substrate 101 is shown. The backside surface 208 may be a surface opposite to the frontside surface 102. The backside surface 208 corresponds to a second surface of the substrate 101.

The backside surface 208 may be parallel to the frontside surface 102. This is shown in FIGS. 2a, 2c, and 2d.

In another embodiment the backside surface 208 may be opposite to the frontside surface 102 but not parallel to the frontside surface 102. This is shown in FIG. 2b.

The backside surface may as well have completely different shapes. Thus, the backside of the surface-structured device 100 may be adapted to the requirements of the usage. In one embodiment the surface-structured device 100 may be used as an inlay and the backside surface 208 may be structured to avoid sliding on a receiving surface by a high roughness or by a key-hole relation between the back-side surface pattern and the receiving surface.

In FIGS. 2c and 2d, backside protrusions 209 are shown on the backside surface 208. The backside protrusions 209, their arrangement in patterns, their arrangement in groups in different areas on the backside surface 208 and any other property may be realized corresponding to the description of the protrusions 103 on the frontside surface 102. The backside surface 208 may as well be realized corresponding to the description of the frontside surface 102.

Further, the positioning of the backside protrusions 209 may be mirror symmetrical to the protrusions 103 on the frontside surface 102. This is shown in FIG. 2d.

Further, the backside surface 208 may be mirror symmetrical to the frontside surface 102. This is shown in FIG. 2d.

Figure 3A:
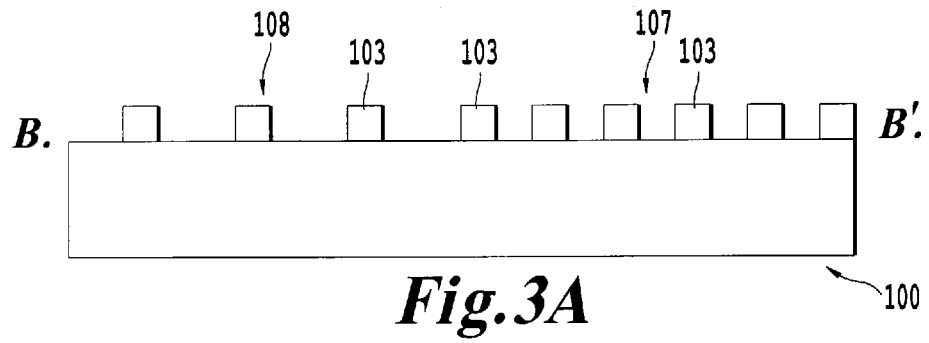
FIGS. 3a and 3b show schematically different embodiments in a vertical cut along the line indicated by B-B' in FIG. 1.
Figure 3B:
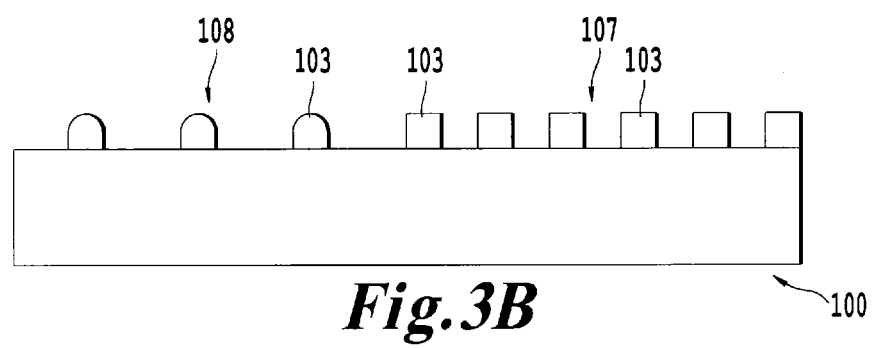

In FIGS. 3a and 3b showing a vertical cut along the line indicated in FIG. 1 by B and B', different embodiments of the surface-structured device 100 with different three-dimensional structures of the protrusions 103 are shown.

The protrusions may have a cylindrical shape as shown for the protrusions 103 in the left part in FIG. 3a. The protrusions 103 may as well have a prism shape as shown for the protrusions 103 in the right part in FIG. 3a and FIG. 3b. The protrusions may have a hemispherical shape as shown for the protrusions 103 in the left part in FIG. 3b. The corners of the three-dimensional shapes may as well be rounded. Further, the protrusions may have a three-dimensional shape with 6 surfaces, where the opposing surfaces are parallel and the adjacent surfaces are perpendicular to each other.

The shape of the protrusions 103 may be identical within an area 107, 108 with a regular pattern.

Selecting an appropriate three-dimensional shape of the protrusions may have an impact on the interaction with the biological sample, and, therefore, the three-dimensional shape represents a further parameter, which may be selected to optimize any of the life-science methods described above. Another effect of the three-dimensional shape of the protrusions may be the velocity with which a liquid of the biological sample may flow over the surface-structure device.

Figure 4A:
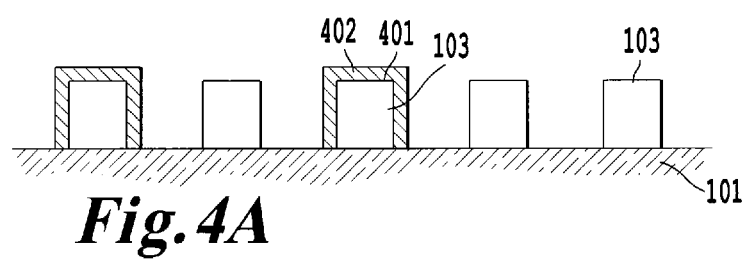
FIGS. 4a to 4c show schematically embodiments having a functionalizing surface layer.
Figure 4B:
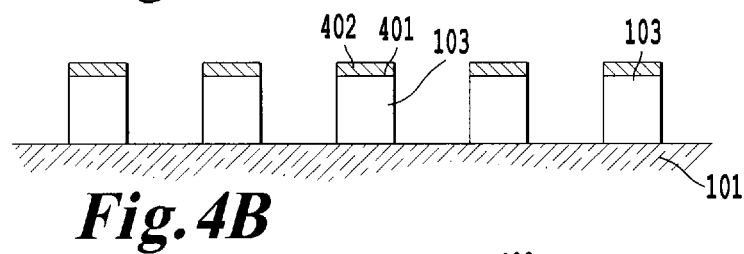

FIG. 4a and FIG. 4b show schematically embodiments with protrusions 103 with a functionalized surface 401. This functionalized surface 401 may be covered by a functionalizing layer 402. This functionalizing layer 402 may be provided on all protrusions 103. Different protrusions 103 may have different functionalizing layers 402. In this case, preferably, protrusions 103 with a first functionalizing layer and protrusions 103 with a second functionalizing layer are arranged in different areas on the surface of the substrate 101. The functionalizing layer 402 may be different for at least two planar areas with different regular patterns and/or different pattern heights. Thus, the effect of the regular pattern and of the functionalizing surface 402 may be combined, thus generating an even more specific interaction of predefined areas on the biological sample material may be achieved. This effect may have even an synergetic effect, thus, may be even larger than the pure addition of the effect of the interaction with the protrusions and the effect of the interaction with the functionalizing surface.

The functionalizing layer 402 may be provided on the entire surface of the protrusions 103 as shown in FIG. 4a or on a part of the surface of the protrusions 103 as shown in FIG. 4b. This part may be a plane surface on top of the protrusions 103.

Figure 4C:
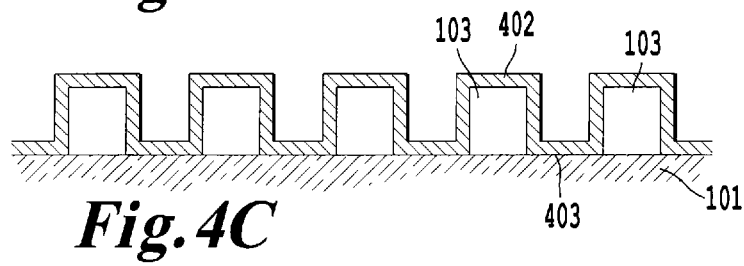

The functionalizing layer 402 may as well cover the surface between the protrusions, i.e. surface 403 between the protrusions 103 and the surface of the protrusions 103 as shown in FIG. 4c. In a further embodiment the functionalizing layer 402 may cover the complete surface including the surface of the protrusions and the area between the protrusions of at least one planar area with the protrusions 103 arranged in a regular pattern. In another embodiment the complete surface including the surface of the protrusions and the area between the protrusions of the frontside and/or backside of the surface-structured device 101 may be covered with a functionalizing layer 402. Thus, there is no restriction where to position the functionalizing layer 402 on the surface of the surface-structured device.

The functionalizing layer 402 may comprise any material adapted to influence the results of a life-science method. This may be a certain chemical functionality influencing the adhesion of the biological material to the surface-structured device 100. The functionalizing layer 402 may comprise metals or polymers. The functionalizing layer 402 may comprise gold or silver or polyglykolamide or an organic material. The functionalizing layer 402 may further be a material that is activated after deposition. The activation may be conducted by UV-activation, plasma-activation or gamma-activation.

In a further embodiment, shown in FIG. 5a, the surface-structured device is an inlay 500, which can be positioned within a vessel 501. The inlay 500 may be positioned in different positions 502, 503 within the vessel 501. The inlay 500 may be positioned on the bottom surface 504 of the vessel. The inlay 500 may as well be positioned in a distance from the bottom surface 504. A vessel 501 with an inlay 500 in a position 503 may have two reaction chambers above and below the inlay 500. Surface-structured devices with protrusions on the frontside and on the backside of the substrate may preferably be used as inlays 500. Such an increase of number of the reaction chambers within one vessel may increase the throughput and may reduce the numbers of vessels 500 needed in a life-science method. Further, such an inlay 500 makes a manufacturing method of the vessel 501 independent from a manufacturing method of the inlay 500.

In a further embodiment, shown in FIG. 5b, the surface-structured device is a vessel 505. Any of the surfaces of the vessel 505 may be the frontside surface 102 with the protrusions 103. Preferably, the frontside surface 102 is the bottom surface of the vessel 505. Thus, in this embodiment the substrate with the frontside surface 102 with the protrusions 103 forms an integral part of the vessel 505 and the protrusions 103 may be directly formed on a surface of the vessel. Thus, the numbers of manufacturing steps may be reduced.

The vessels 501, 505 may be titer plates or micro-titer plates or any other vessel used in life-science methods.

Figure 6:
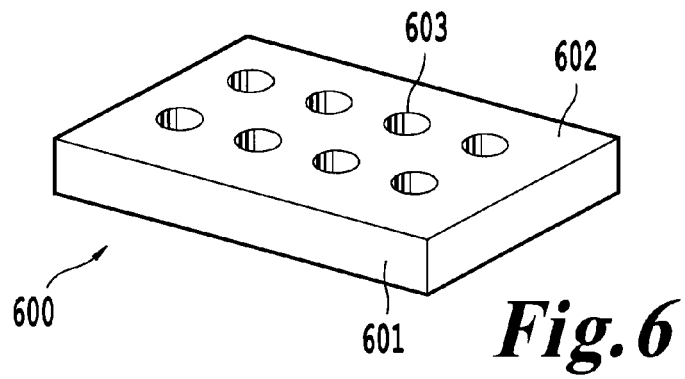
FIG. 6 shows schematically an embodiment of the stamper used to manufacture a surface-structured device.

In FIG. 6 a stamper 600 is shown schematically, which may be used in manufacturfing method of the surface structured device. The stamper may have a body element 601 with at least on planar surface 602. A plurality of holes 603 with openings of the holes 603 in the planar surface 602 may be arranged in the stamper body element 601. A shortest dimension of the opening of the holes 603 may be smaller than 250 nm and the openings of at least a first group of the plurality of holes 603 are arranged in a first regular pattern in a first planar area of the planar surface 602.

The stamper 600 may be a negative of the surface of any of the above-described embodiments of the surface-structured device. Thus, the stamper may be provided as a negative with any dimension of the embodiments of the surface-structured device as described above. The dimensions may vary slightly from the surface-structured device, which is formed by the stamper 600 due to manufacturing method characteristics. For example a shrinking of the protrusion material may occur during the manufacturing method and, therefore, the size of the holes may correspondingly be slightly larger and compensate for this shrinking.

The material may be different from the material of the corresponding surface-structured device. Therefore, the stamper material may be selected only based on the manufacturing process conditions and requirements.

The stamper may be used manifold for the manufacturing of many the surface-structured device.

Figure 7:
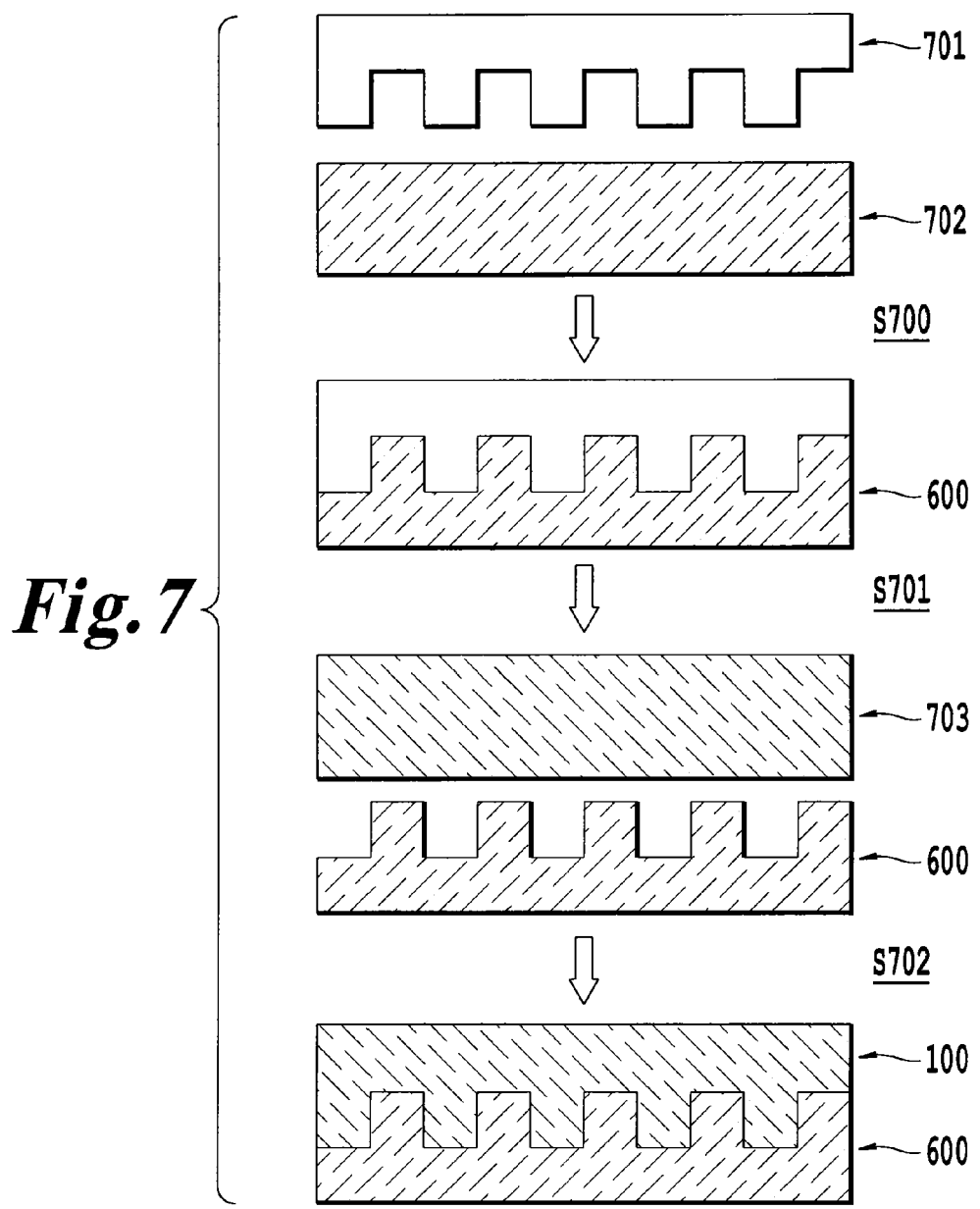
FIG. 7 shows schematically an embodiment of the manufacturing process for the surface-structured device.

FIG. 7 shows a manufacturing method for the surface-structured device 100. In a first step a master device 701 is provided. This master device 701 may have a structure on a surface, which corresponds to at least a part of the structure on the target surface-structured device 100.

The master device 701 may be manufactured by a manufacturing method as described in the U.S. patent application Ser. No. 12/323,220 which is included as reference herewith. The manufacturing method of the master device 701 may correspond to the phase-transition mastering (PTM) manufacturing method of the master disc as described in [0058] to [0066] in U.S. application Ser. No. 12/323,220.

In a step S700, the surface of the master device 701 carrying the structure may be pressed into a moldable material 702, thus the structure is mapped as a negative in the moldable material 702. Subsequently the master device 701 may be separated from the structured moldable material. The structured moldable material corresponds to the stamper 600 in FIG. 6. The stamper may be further modified to optimize its properties to the manufacturing method of the surface-structured device 100.

In a step S701 the stamper 600 may be brought in the vicinity of a body of material 703.

In a first embodiment of the manufacturing method the material of the body 703 may be moldable at least on a surface and the stamper 600 may be pressed in the body 703 at S702. Thus, the structure on the stamper 600 may be transferred in a corresponding structure in the body 703.

This structured body corresponds to the surface-structured device 100 and the structure of the surface-structured device 100 substantially corresponds to the structure on the master device 703.

Subsequently, the stamper 600 may be separated from the surface-structured device 100 and further manipulation steps of the surface-structured device may follow.

In a second embodiment of the manufacturing method the material of the body 703 corresponds to the substrate layer material and a slit may be kept between the surface of the substrate layer and the stamper 600.

In a subsequent step fluid material may be pressed into the slit and all holes on the stamper 600 and the slit are filled with the fluid material. Then the fluid is hardened.

Subsequently, the stamper 600 may be separated from the surface-structured device 100 and further manipulation steps of the surface-structured device may follow.

In another embodiment any of manufacturing methods may be repeated with differently structured master device by forming different structures on one body 703 based on differently structured stampers. Each stamper may have a plurality of holes which form a plurality of groups. Each group may form a different regular pattern.

The body 703 may have one planar surface. Alternatively the surface may be provided with planar areas being parallel to each other but not being within one plane.

The structure of the surface-structured device 100 substantially corresponds to the structure on the master device 701. Modification of the structures on the stamper may lead to deviations between the structure of the surface-structured device 100 and the structure of the master device 701.

In another embodiment of a manufacturing method of the stamper, the stamper may be manufactured by a fluid material analogous to the manufacturing method of the surface structured-device with a fluid material.

The steps of pressing the stamper in the moldable material or filling the fluid material in the slit and hardening the fluid material followed by separating the stamper from the surface-structured device may be repeated multiple times. However, some abrasion may be take place. If the abrasion has reached a certain level, the stamper may be exchanged by a new stamper, which may be manufactured based on the same master device.

Thus, an manufacturing method is provided which may have a certain tolerance to abrasion and, therefore, a higher thoughput and a lower cost, may be achieved.

In the description of the manufacturing methods the term structured/structure does refer to both the regular pattern, but as well to the shape of the protrusions.

The invention claimed is:

1. A surface-structured device for life-sciences comprising:
    a substrate having a frontside surface and a backside surface opposite the frontside surface;
    a plurality of groups of first protrusions arranged on the frontside surface; and
    a plurality of second protrusions arranged on the backside surface of the substrate; wherein
    a shortest dimension of each of the first protrusions in the plurality of groups at a junction of the first protrusion and the frontside surface is smaller than 250 nm;
    each of the groups of first protrusions is formed in corresponding different areas of the frontside surface; and
    each group of the first protrusions is arranged on respective planar areas of the frontside surface in respective different regular patterns in respective planes of the corresponding different areas;
    at least a first group of the plurality of second protrusions arranged on the backside surface is arranged on a planar area of the backside surface in a regular pattern in a plane of the planar area of the backside surface; and
    a shortest dimension of each of the second protrusions at a junction of the second protrusion and the backside surface is smaller than 250 nm.

2. The surface-structured device according to claim 1, wherein each of the different areas is planar and parallel to a first planar area.

3. The surface-structured device according to claim 1, wherein the areas with regular patterns have a size of at least 1000 mm².

4. The surface-structured device according to claim 1, wherein a material of each of the first and second protrusions and a material of the substrate have a same composition at the junction of the first protrusion and the frontside surface and the junction of the second protrusion and the backside surface of the substrate.

5. The surface-structured device according to claim 1, wherein first protrusions of at least one group of the first protrusions are of same dimensions.

6. The surface-structured device according to claim 1, wherein each of the first protrusions has one of a quadratic, a rectangular, a rectangular with rounded corners, an oval and a round footprint at the junction to the substrate.

7. The surface-structured device according to claim 1, wherein each of the first protrusions has one of a hemispherical shape, a prism shape, and a prism shape with rounded corners with a height between 10 nm and 100 nm.

8. The surface-structured device according claim 1, wherein
    at least one of the groups of first protrusions is arranged in at least two sub-areas of a corresponding first area or further areas; and
    a height of the first protrusions in a first sub-area of the at least two sub-areas is different from a height of the first protrusions in a second sub-area of the at least two sub-areas; and
    the first protrusions of the at least one group belonging to a same sub-area have a same height.

9. The surface-structured device according to claim 1, wherein
    at least two of the planar areas are located in different planes; and
    tops of corresponding first protrusions arranged in the two areas are located within one plane.

10. The surface-structured device according to claim 1, wherein a size of an opening between two first protrusions of at least one planar area of the frontside surface ranges from 1 to 10 times the shortest dimension of the two first protrusions.

11. The surface-structured device according to claim 1, wherein a core of the first protrusions comprises one of a polymer, a treated polymer, a metal, and an alloy.

12. The surface-structured device according to claim 1, wherein
    at least one first protrusion has a core material and a surface material,
    said surface material of the at least one first protrusion and said core material of the at least one first protrusion having a different constitution, and wherein the surface material provides a different functionality than the core material.

13. The surface-structured device according to claim 1, wherein
    the substrate is adapted to form a wall of a vessel or is located between two reaction chambers of the vessel.

14. A surface-structured device for life-sciences comprising:
    a substrate having a frontside surface; and
    a plurality of first protrusions arranged on the frontside surface; wherein
    a shortest dimension of each of the first protrusions at a junction of the first protrusion and the frontside surface is smaller than 250 nm; and
    at least a first group of the plurality of first protrusions is arranged on a first planar area of the frontside surface in a first regular pattern in a plane of the first planar area of the frontside surface,
    the surface-structured device further comprising:
    a plurality of second protrusions arranged on a backside surface of the substrate opposite to the frontside surface; wherein
    at least a first group of the second protrusions is arranged on a planar area of the backside surface in a regular pattern in a plane of the planar area of the backside surface; and
    a shortest dimension of each of the second protrusions at a junction from the second protrusion to the backside surface is smaller than 250 nm.

* * * * *